US005130257A

United States Patent [19]
Baer et al.

[11] Patent Number: 5,130,257
[45] Date of Patent: Jul. 14, 1992

[54] CHEMICAL SENSOR UTILIZING A SURFACE TRANSVERSE WAVE DEVICE

[75] Inventors: Richard L. Baer, Los Altos; Carl Myerholtz, Cupertino; Curt Flory, Menlo Park; May Tom-Moy, San Carlos, all of Calif.

[73] Assignee: Hewlett-Packard Company, Palo Alto, Calif.

[21] Appl. No.: 251,149

[22] Filed: Sep. 29, 1988

[51] Int. Cl.⁵ .................... G01N 27/416; C12M 1/34
[52] U.S. Cl. .................... 436/151; 435/288; 435/291; 204/403; 73/DIG. 4
[58] Field of Search .............. 436/151; 435/288, 817; 204/403, 416; 73/DIG. 4

[56] References Cited

U.S. PATENT DOCUMENTS

| | | | |
|---|---|---|---|
| 4,312,228 | 1/1982 | Wohltjen | 73/597 |
| 4,735,906 | 4/1988 | Bastiaans | 436/527 |
| 4,767,719 | 8/1988 | Finlan | 436/501 |
| 4,789,804 | 11/1988 | Karube et al. | 310/311 |
| 4,847,193 | 7/1989 | Richards et al. | 435/6 |

FOREIGN PATENT DOCUMENTS 0246846 5/1987
89309266 10/1990 European Pat. Off.

OTHER PUBLICATIONS

Thompson et al., Ultrson. Symp. Proc. (1), pp. 261-266, 1986, in Chemical Abstract (22), 210466k.
Daniel F. Thompson, et al, "Surface Transverse Wave Propagation" 1986 Ultrasonics Symposium, pp. 261-266.
Calabrese et al, "Surface Acoustic Wave Devices as Chemical ..." Anal. Chem. 1987, 59, pp. 833-837.
Donald L. Lee, "A Theoretical Analysis of Surface Skimming ..." Proc. 1978 IEEE Ultrasonics Symposium, pp. 675-679.
Shiokawa, S. & Moriizumi, "Design of SAW Sensor in Liquid" Proceedings of the 8th Symposium on Ultrasonic Electronics, Dec. 8-10, 1988, 27 Mar. 1988, Suppl. 27-1, Tokyo, Japan; pp. 142-144.
T. Moriizumi, et al. "New Sensor in Liquid Using Leaky Saw", 1987 Ultrasonics Symposium pp. 579-582, Oct. 14-16, 1987.
C. A. Flory and R. L. Baer, "Surface Transverse Wave ..." Proc. 1987 IEEE Ultrasonics Symposium, pp. 313-318.

Primary Examiner—James C. Housel
Assistant Examiner—William Ky Chan

[57] ABSTRACT

A sensor (11, 12, 13, 15) suitable for use as a viscosity sensor, a chemically selective sensor, or a chemically specific sensor. The sensor (11, 12, 13, 15) is a surface transverse wave (STW) device that, for solute concentration measurements, includes a binding layer (18) selected to bind to the solute to be measured. This binding layer (18) can be an antibody so that the sensor detects a particular antigen.

16 Claims, 6 Drawing Sheets

CHEMICAL SENSOR UTILIZING A SURFACE TRANSVERSE WAVE DEVICE

FIELD OF THE INVENTION

This invention relates in general to chemical sensors and relates more particularly to a chemical sensor utilizing a surface transverse wave device. In the following, the first digit of a reference numeral will indicate the first figure in which is presented the element referenced by that reference numeral.

BACKGROUND OF THE INVENTION

Piezoelectric resonators have been used as microgravimetric immunoassay devices (See, for example, Joy E. Roederer and Glenn J. Bastiaans, "Microgravimetric Immunoassay with Piezoelectric Crystals", Anal. Chem. 1983, 2333-2336). Changes in the amount of mass attached to the surface cause shifts in the resonant frequency. Selective mass detection is achieved by coating the surface of the piezoelectric crystal with a substance that preferentially binds to the substance to be detected. For example, when specific antibodies are bound to the crystal surface, they selectively bind to their corresponding antigen. The concentration of the antigen in a fluid can be measured by immersing the sensor and inferring the change in mass from the change in resonant frequency.

The mass sensitivity (i.e., the fractional frequency change divided by the causative surface mass density change) increases as the mass of a bulk wave resonator is decreased or, correspondingly, as the resonator thickness is decreased. A practical lower limit of about 100 microns, corresponding to a resonance frequency of about 20 MHz, is imposed on resonator thickness by manufacturing difficulties. Consequently the sensitivity of a bulk wave resonator sensor is limited.

Acoustic waveguide devices have also been used as mass sensors. Mass attached to the surface of the waveguide will produce a phase shift in the output signal from the waveguide. The concentration of the antigen can be determined from this phase shift. These devices can utilize different wave motions, including Rayleigh waves (SAWs), Lamb waves, surface transverse waves (STWs) and surface-skimming bulk waves (SSBWs). In Rayleigh and Lamb wave devices, the predominant component of particle motion due to acoustic displacement is normal to the surface of the waveguide and is thereby also normal to the direction of propagation. In STW devices, the predominant particle velocity component due to acoustic displacement is parallel to the surface and normal to the propagation direction. SSBWs have the same dominant particle velocity direction as STWs, but the acoustic waves are not trapped at the surface, as is the case in STWs, and therefor diffract into the substrate.

The particle velocity direction due to acoustic displacement has a strong influence on the behavior of the device when immersed in a fluid. The acoustic wave propagation velocity varies as the square root of the ratio of the aggregate stiffness to the aggregate mass of the waveguide. The addition of mass to the surface of a waveguide decreases the propagation velocity, which causes a corresponding change in the net phase shift across the device. The phase shift can be measured directly, or inferred from measurements of the frequency of an oscillator containing the surface acoustic wave device as a feedback element.

In a surface wave device, since the wave is trapped within a region near the surface of the device, the response of this wave to additional mass on the surface is dependent only on the amount of mass within the region within which the wave is trapped. Therefore, the fractional mass sensitivity of a surface wave device is a function of the penetration depth of the wave into the waveguide instead of the substrate thickness.

The penetration depth ranges from a fraction of an acoustic wavelength to a few acoustic wavelengths, depending on the characteristics of the device and the type of wave motion. Because acoustic waveguide devices can be easily fabricated at frequencies of up to several gigahertz using standard photolithographic techniques, the penetration depths can be reduced to the order of several microns, thereby making these devices very sensitive.

Although the fractional frequency (or phase) change induced in an acoustic waveguide device is strictly a function of the penetration depth of the wave, the phase change is proportional to the length of the device. The optimum length depends on the degree of wave attenuation. This sensitivity dependence on length provides a further sensitivity advantage over a bulk wave resonator.

SAW devices make poor chemical sensors in applications which require the immersion of the sensor in a liquid because the dominant acoustic displacement component couples strongly to compressional waves in the fluid. The reason for this is as follows. Since the acoustic propagation velocities of Rayleigh waves in solids are almost universally higher than the velocities of compressional waves in liquids, there always exists a direction of radiated acoustic waves in the liquid that at the surface of the waveguide are in phase with the Rayleigh mode of the SAW device. Consequently energy will radiate away from the SAW device into the fluid, causing an unacceptable amount of insertion loss.

Lamb wave devices also make poor chemical sensors for a related reason (See, for example, R. M. White, P. J. Wicker, S. M. Wenzel, and E. T. Zellers, "Plate Mode Ultrasonic Oscillator Sensors", IEEE Trans., vol. UFFC-34, #2, pp. 163.). Lamb wave devices have the same dominant acoustic particle velocity component as SAW devices. However, by decreasing the thickness of the waveguide, the velocity of the mode can be caused to fall below that of the surrounding fluid. This prevents phase matching and hence prevents the radiation of energy into the liquid. Unfortunately, this decreased thickness also causes the velocity of the Lamb wave to be a strong function of the density of the fluid. This effect masks the mass sensitivity of the sensor. In addition, the difficulties of fabricating a thin waveguide limit the maximum frequency of a Lamb wave device to several Megahertz, thereby limiting the sensitivity of such a device. STW devices do not suffer from these limitations, as the summary of the invention will show.

SUMMARY OF THE INVENTION

In accordance with the illustrated preferred embodiment, a method of testing a liquid is presented. In accordance with the disclosed method, a surface transverse wave (STW) device is immersed in a liquid under test, a signal is applied to the STW device and the phase or frequency of an output signal from the STW device is monitored. When the STW device is coated with an adhesion layer that is selective for a preselected solute, then this method measures the concentration of such solute in the liquid solution. When the STW device has no such adhesion layer, it measures the viscosity of the liquid.

An STW sensor is also presented that is suitable for use as a chemical sensor in liquid solutions. This sensor utilizes a surface transverse wave (STW) in a piezoelectric crystal to detect a change in mass attached to the surface of the crystal. Because such a wave has no displacement component normal to the surface, there is no coupling to compressional waves in the liquid. The only mechanism by which energy is lost to the liquid is through shear viscosity. Since the liquids of interest for chemical sensing have low shear viscosities, the attenuation of the STW mode is several orders of magnitude lower than that due to radiation in a SAW mode. It is also much lower than that due to the diffraction of an SSBW mode.

An STW device consists of a piezoelectric substrate, one or more transducers (typically interdigital transducers (IDTs)) and gratings or plates which trap the mode to the surface of the substrate. A plate-based surface transverse wave waveguide is also known as a Love waveguide. In a 1-port STW device, an IDT is surrounded by two reflective gratings. The grating and IDT characteristics and the spacing of the gratings determines the resonance frequency. In a 2-port STW device, one IDT serves as the input and another as the output, with a grating or plate covering the gap between the two.

The IDTs and gratings or plates are deposited on the surface of the substrate using photolithographic techniques. In an STW device the grating or plate is required in order to trap the transverse wave mode to the surface. The mass loading by this grating or plate reduces the wave velocity at the substrate surface, thereby acting to trap this wave mode. In addition, when the grating or plate is conductive, it shorts out the electric field at the surface of the substrate, thereby reducing the piezoelectric stiffness of the substrate at the surface and further reducing the wave velocity at the surface. In the absence of the grating/plate this mode diffracts into the substrate, resulting in high attenuation. The mass loading and electrical shorting produced by the addition of a conductive grating/plate traps the wave and prevents excess attenuation. The grating provides stronger trapping than the plate, for equivalent thicknesses and densities. Waves that are more strongly trapped have shallower penetration depths and greater electrical coupling and mass sensitivity.

When this sensor is used in liquids with a high dielectric constant, the liquid can effectively short each of the IDTs, thereby strongly degrading electrical coupling into and out of the sensor. To avoid this, the electrodes are protected by a low dielectric coating. The grating elements can also be shorted together with bussbars or formed of a nonconductive substance to eliminate such sensitivity to the dielectric properties of the liquid.

Because the coupling to longitudinal acoustic modes in the fluid has been eliminated, this sensor is sensitive enough to measure the viscosity of the fluid. To serve as a chemical sensor, on top of the top surface is applied an additional layer that selectively binds to a chemical class of interest. When such a sensor is immersed in a fluid containing chemicals in this class, such chemicals bind to the surface of the sensor thereby increasing the mass loading of this top surface. For example, antibodies can be bound to the top surface of the sensor, whereby this sensor is chemically specific for the corresponding antigens.

DESCRIPTION OF THE PREFERRED EMBODIMENT

Figure 1:
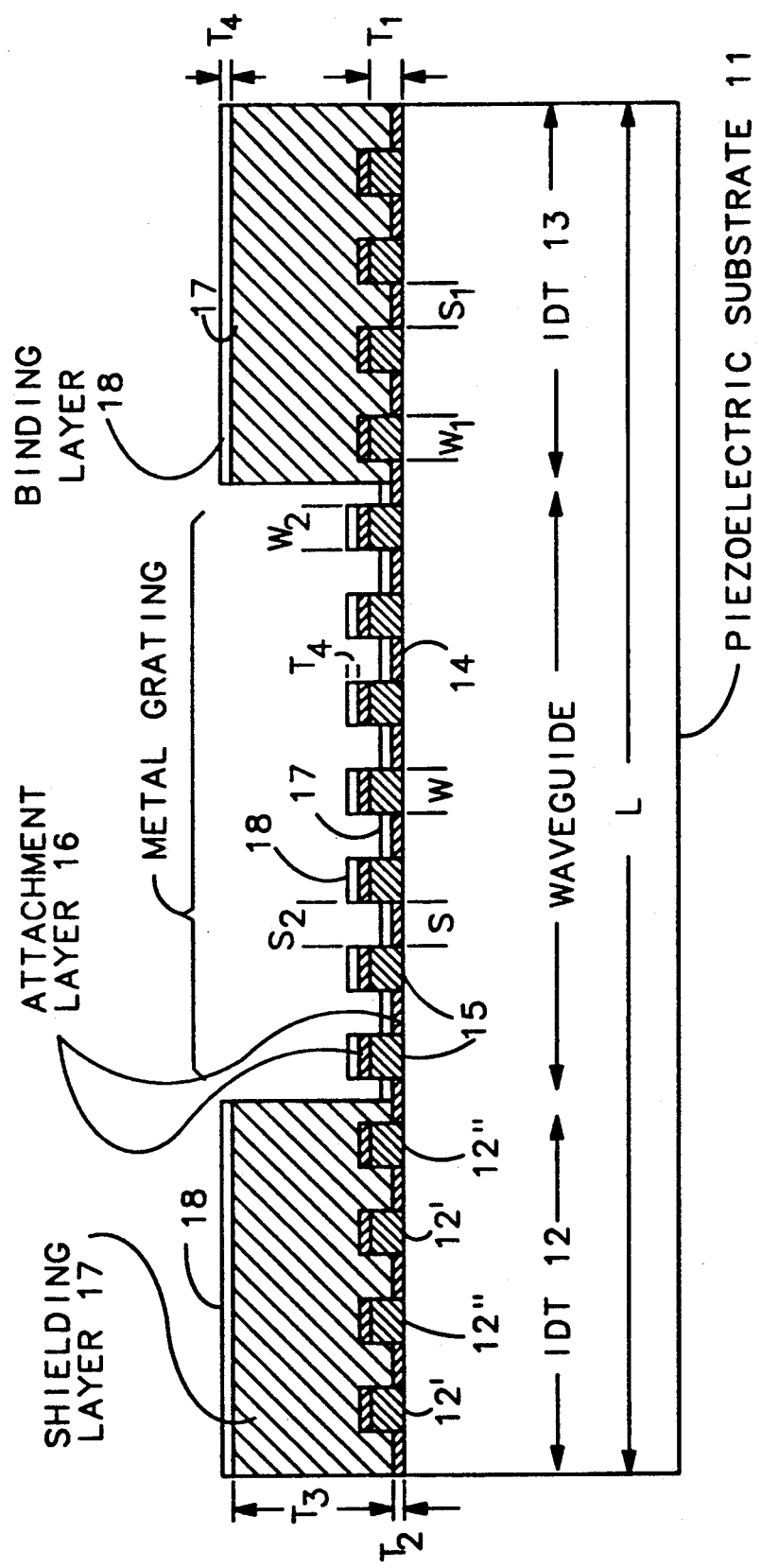
FIG. 1 is a side cross section of a surface transverse wave (STW) waveguide sensor that is suitable for use as a viscosity sensor and/or a chemical sensor.
Figure 4:
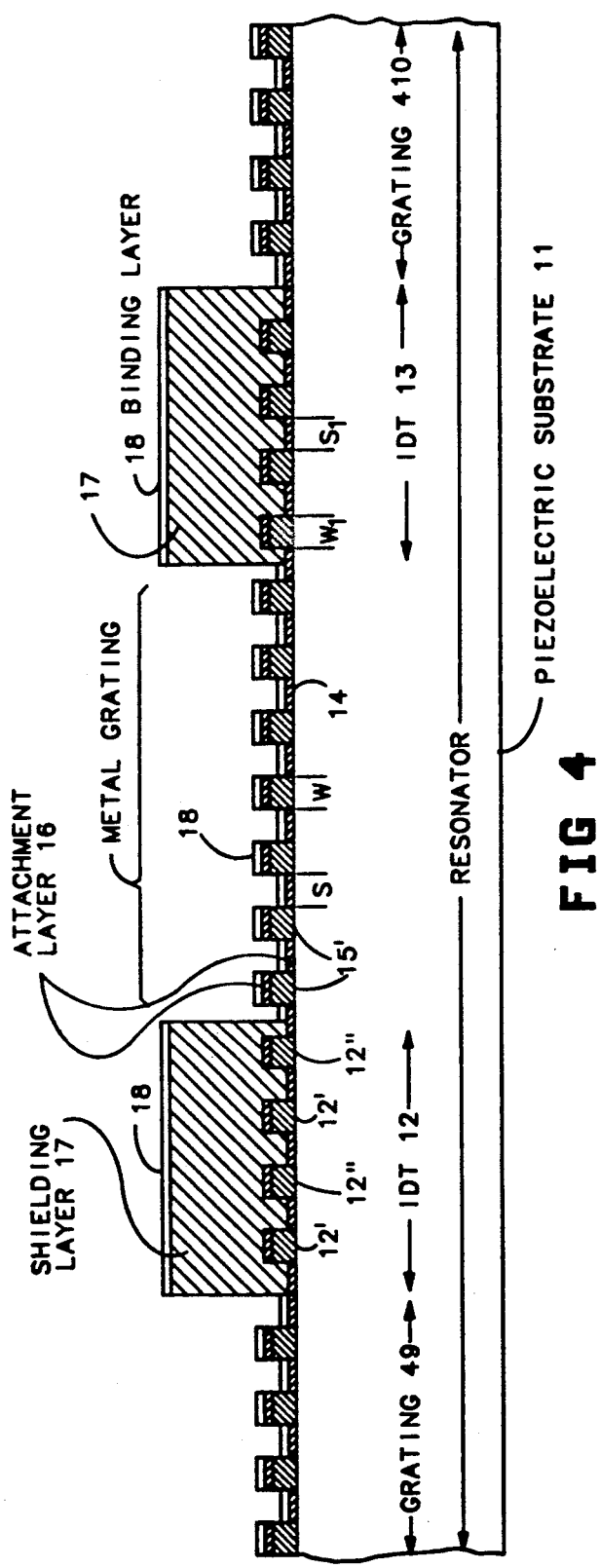
FIG. 4 is a side cross section of a surface transverse wave 2-port resonator sensor that is suitable for use as a viscosity sensor and/or a chemical sensor.

In FIG. 1, on a piezoelectric substrate 11, such as quartz or lithium niobate (LiNbO3), are formed an input transducer, such as interdigital transducer (IDT) 12 having electrodes 12' and 12'', and an output transducer, such as interdigital transducer (IDT) 13. These IDTs have a typical thickness $T_1$ on the order of 0.1–1.0 micron, a width $W_1$ on the order of 1–100 microns and a spacing $S_1$ on the order of 1–100 microns. Reflective gratings 49 and 410 in FIG. 4 are optionally placed at the outside edge of each IDT in order to form a 2-port resonator. These transducers and gratings can be formed by well known photolithographic techniques.

In general, the material chosen for substrate 11 must be piezoelectric and have specific crystal cuts that enable trapping of surface transverse waves at a surface of the substrate, and should: (1) exhibit low acoustic loss (i.e., have low viscous attenuation); (2) have a high dielectric constant and high electromechanical coupling constant to minimize the parasitic electrical effects of fluid loading upon the transducer; and (3) have a low variation of velocity with temperature. Quartz has the advantage of exhibiting a low temperature variation of the acoustic velocity. Lithium Niobate has the advantage of better piezoelectric coupling to IDTs 12 and 13. The ST-cut of Quartz (typically used for SAW devices) can be used for STW devices by rotating the propagation direction 90 degrees (See, for example, D. F. Thompson and B. A. Auld, "Surface Transverse Wave Propagation Under Metal Strip Gratings", 1986 Ultrasonics Symp. Proc., IEEE Cat. #86CH2375-4, pp. 261.). The IDTs can be formed by the deposition of aluminum, gold or a metal alloy.

Figure 2:
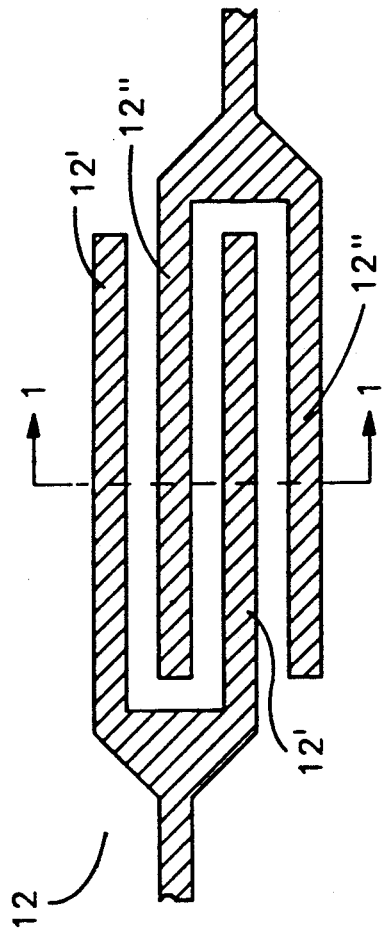
FIG. 2 is a top view of a typical IDT.

A top view of transducer 12 is shown in FIG. 2, illustrating the relationship between electrodes 12' and 12''. An applied voltage difference between electrodes 12' and 123" produces between these electrodes an electric field that interacts electromechanically with the piezoelectric substrate. On top of surface 14, between IDTs 12 and 13 is formed a metal grating 15 having element width $W_2$ and spacing $S_2$ comparable to the width and spacing of IDTs 12 and 13. This grating traps the transverse acoustic wave to the surface of the substrate. The fingers of the grating can be shorted together with buss-bars to minimize the dielectric effects of the fluid on the performance of the detector.

An attachment layer 16 can be deposited (e.g., by sputtering or evaporation) on top of elements 12, 13 and 14. Layer 16 should bind strongly and be hermetic to protect elements 11-15 from attack by chemicals. This layer has a thickness $T_2$ on the order of 10-1,000 Angstroms. For embodiments to serve as a chemical sensor, layer 16 is selected to provide a good binding surface for a chemically selective binding layer 18 to be deposited over grating 15. Silicon dioxide ($SiO_2$) is a good choice because there exists a large amount of literature on binding various chemically selective compounds to $SiO_2$. Layer 18 typically has a thickness $T_4$ on the order of a monolayer (for an antibody binding layer) to several microns.

A thick shielding layer 17 is deposited over IDTs 12 and 13. This shielding layer serves a dual purpose. First, it should form a hermetic seal over the IDTs to protect them from corrosion. Second, it should prevent substantial shorting of the electrodes of the IDTs. When used as a chemical sensor in any water-based solution, IDTs will be exposed to the influence of such water solvent. Since water has a relatively high dielectric constant (on the order of 75), it can capacitively short out the electrodes of the IDTs. To prevent this, layer 17 must be thick enough (i.e., have a thickness $T_3$ on the order of or larger than the electrode spacing in the IDT) to prevent the water from substantially drawing the electric fields from the IDT electrodes out of substrate 11. For fabrication ease, layer 17 should also be easily patterned lithographically. One possible choice for layer 17 is silicone rubber.

For a phase sensitive detector, the amount of phase shift is substantially proportional to the length L of the device. On the other hand, the strength of the signal at output transducer 13 is a decreasing exponential function of L. Thus, because of attenuation due to viscosity, the signal to noise ratio varies as a decreasing exponential function of L. The balance between these competing effects is that the detector should have a length L on the order of the inverse of the amplitude attenuation factor (in nepers/meter).

The particular choice of binding layer 18 will depend on the class of chemicals that are to be detected by this chemical sensor. In general, it should bind strongly to attachment layer 16 and must bind selectively to the class of chemicals to be detected. Many such chemicals are known from the fields of gas and liquid chromatography. For example, the gas chromatography (GC) and liquid chromatography (LC) stationary phases are selective for a class of chemicals, but are not specific for a single chemical. In addition, when binding layer 18 is an antibody, it will be highly chemically specific to the antigen that binds to that antibody. In response to an antigen, the immune system of an animal generates an assortment of antibody molecules (each referred to as a monoclonal antibody) to different parts of an antigen, each molecule derived from a single clone of antibody producing cells. This mixture of monoclonal antibodies is referred to as polyclonal antibodies. Binding layer 18 can thus be either a monoclonal antibody or a polyclonal antibody. Typically, the bond formed between binding layer 18 and the chemical for which it is selective will be noncovalent. In biological applications, these noncovalent bonds are usually ionic bonds, hydrogen bonds and van der Waals bonds.

Binding layer 18 should also form a stiff linkage between attachment layer 16 and the chemical to be detected. As the stiffness of this linkage decreases, the effect of mass loading on the acoustic wave propagation velocity decreases, thereby also decreasing the sensitivity of the sensor. Thus, the required minimum stiffness and the sensitivity of associated of this linkage is determined by the desired device sensitivity electronics that detects a frequency shift or phase delay generated by this mass loading.

This STW sensor can be used with nucleic acid probes. In this application, the binding layer consists of identical molecules that are each a fragment of one strand of a nucleic acid. In a nucleic acid, each of these strands is covalently bonded to a complementary strand fragment. Therefor, this sensor detects the concentration of this complementary strand fragment in the liquid under test.

Figure 3:
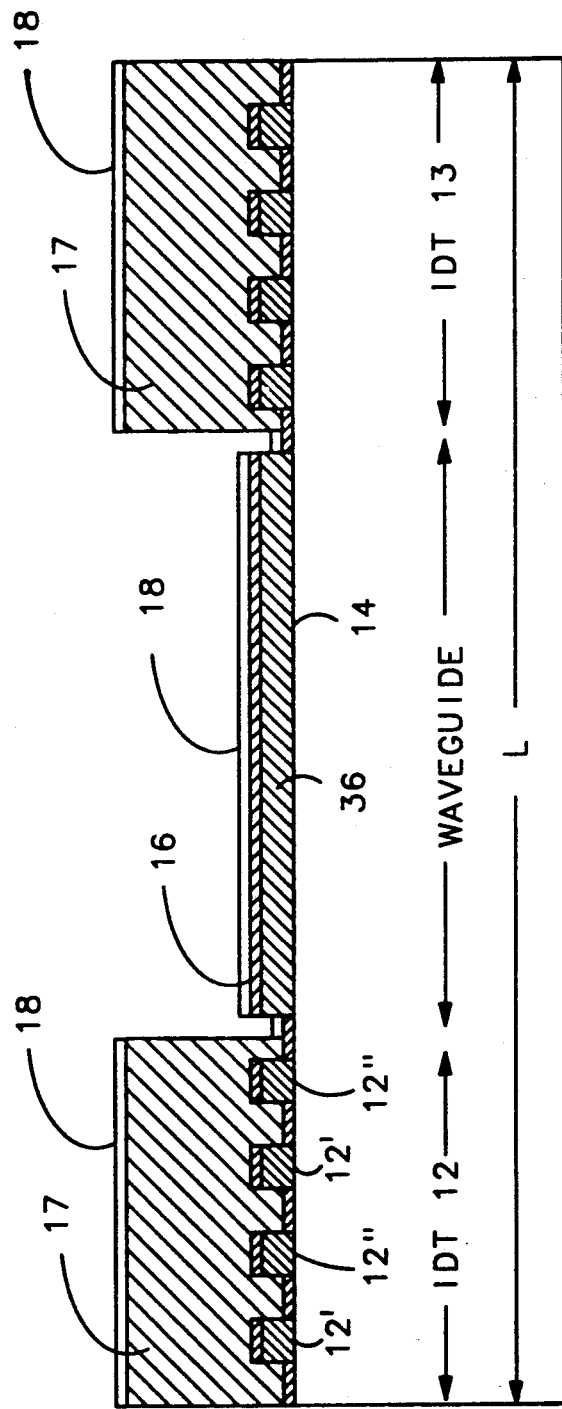
FIG. 3 is a side view of a STW sensor of the same type as in FIG. 1, except that it is mass loaded with a Love plate instead of a metal grating.

If this sensor is to be reusable, the bond between layer 18 and the chemicals to be detected must be reversible by convenient chemical means. In throw-away type sensors, this limitation is not required. Typical dimensions for this device are as follows: 10 mm long and 3 mm wide, on a 0.5 mm thick substrate. In FIG. 3 is shown an alternate embodiment in which grating 15 (of FIG. 1) is replaced by a Love plate 36.

Because the motion of top surface 14 is substantially parallel to this top surface, coupling of this motion into compressional modes in a liquid sample is extremely small. This coupling is so small that it is practical to use this sensor to measure the viscosity of the liquid sample. For a viscosity sensor, layer 16 is used to protect the sensor and layer 18 is not required (since the sensor is not specific in this mode of operation). In this application, the excess insertion loss due to the shear viscosity of the fluid is measured, rather than measuring the phase shift or frequency.

This STW chemical sensor exhibits on the order of $10^7$, $10^3$ and $10^3$ times the sensitivity of the bulk wave, SAW, and Lamb wave devices, respectively, discussed in the Background of the Invention. This increased sensitivity is due in large part to the fact that the STW sensor can operate at frequencies of hundreds of megahertz.

Figure 5:
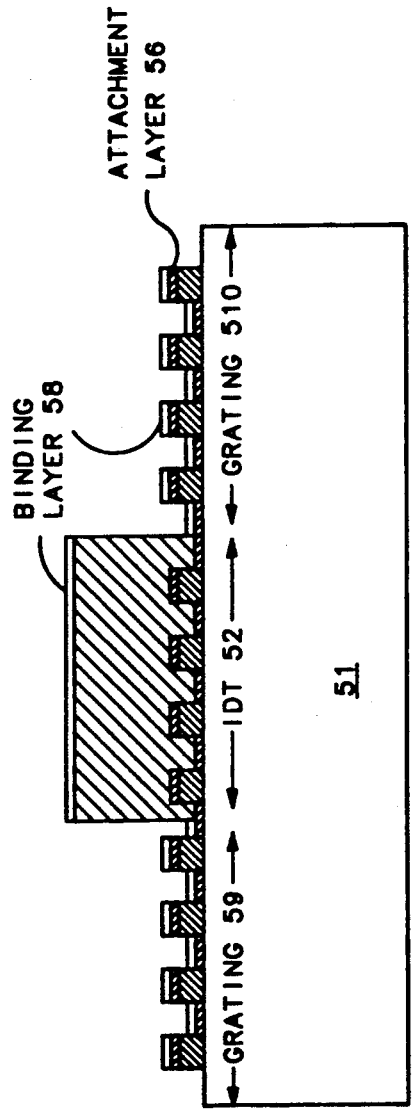
FIG. 5 is a side cross section of a surface transverse wave 1-port resonator sensor that is suitable for use as a viscosity sensor and/or a chemical sensor.

An alternate 1-port resonator embodiment is shown in FIG. 5. In this embodiment, a single IDT 52 is contained between a pair of gratings 59 and 510. Attachment layer 56 and binding layer 58 enable selective binding to a particular solute or class of solutes in the solution under test. These two gratings serve a dual function. They reflect acoustic waves in this device, thereby defining the dimensions of a resonator cavity between these gratings. In addition, they trap the STW wave at the surface so that mass loading of these gratings by the solute that selectively binds to binding layer 58 affects the velocity of the acoustic wave at the top surface of substrate 51, thereby enabling detection of the concentration of this solute by measuring the change in resonant frequency of the device when immersed in the solution under test. In addition to the particular STW embodiments presented herein, there are other well known embodiments of STW devices that can be used as these chemical sensors.

Figure 6:
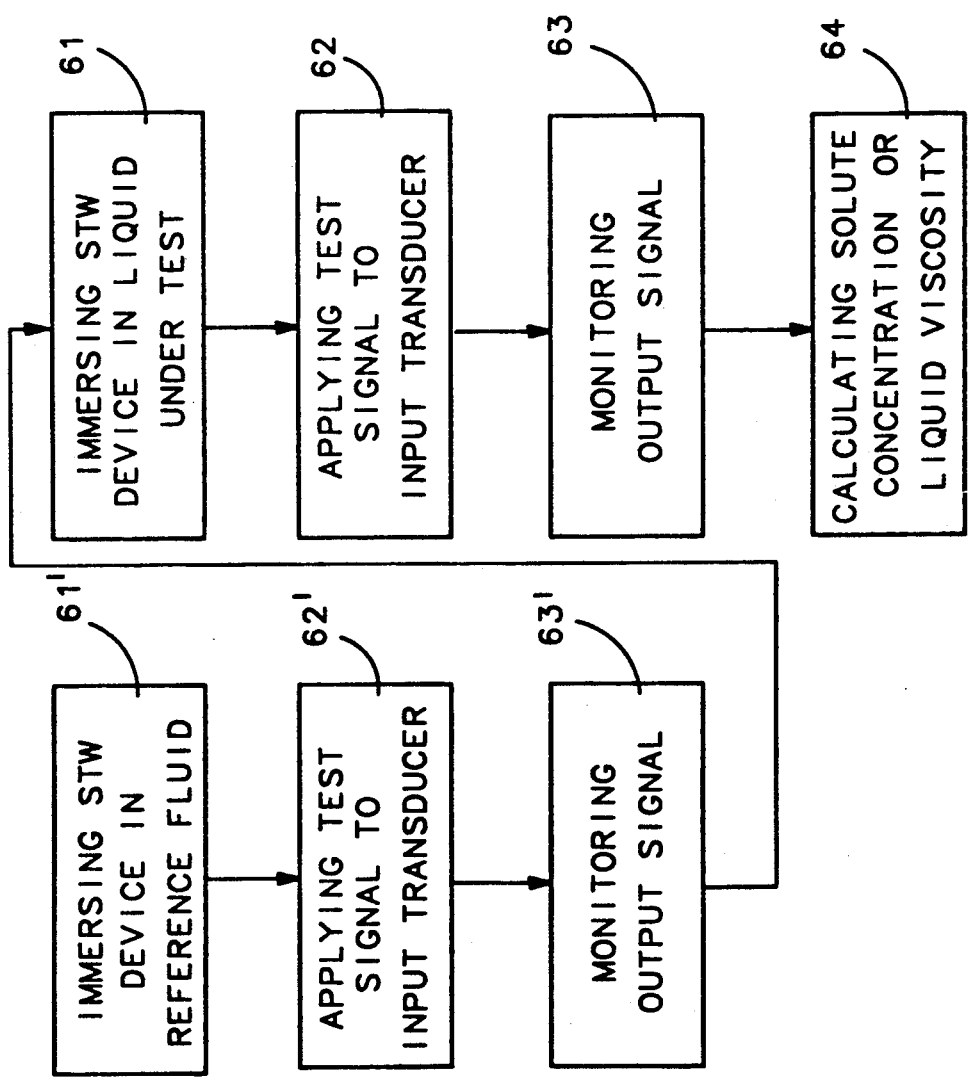
FIG. 6 illustrates the method of measuring a liquids viscosity and/or solute concentration by immersion of an STW device in the liquid.
Figure 9:
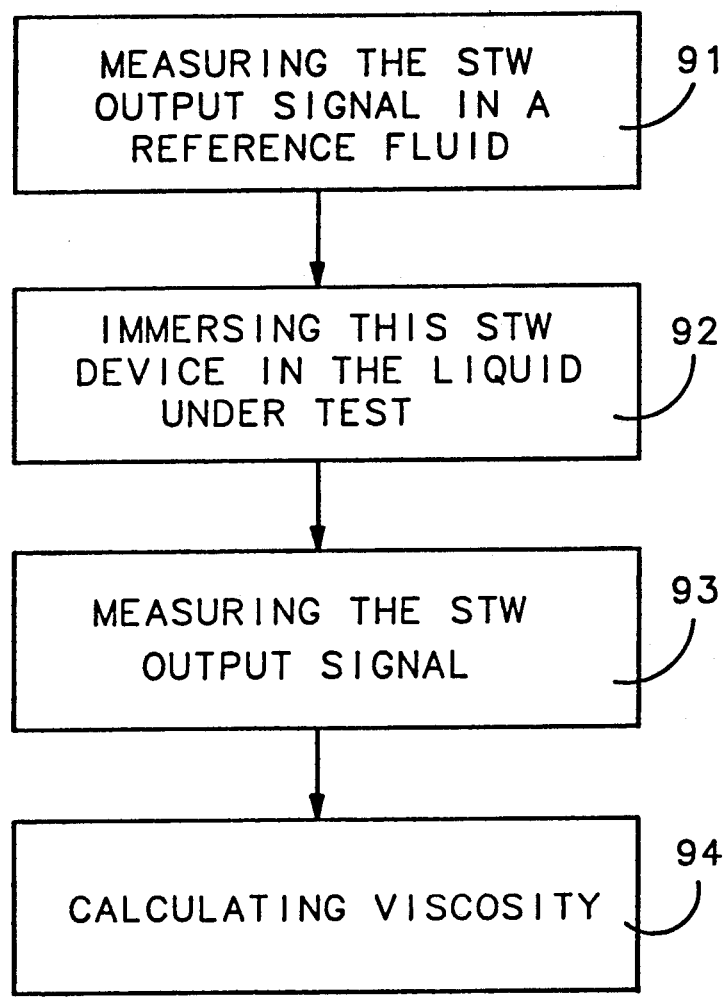
FIG. 9 is a simplified flow diagram of the measurement process of figure.

In FIG. 6 are illustrated the method steps involved in measuring the viscosity or chemical concentration of a liquid. When measuring solute concentration, an STW device, having an attachment layer that bonds selectively to the solute, is immersed (step 61) in the liquid under test. Test signals are applied to an input of the STW device (step 62) and output signals from the STW device are monitored (step 63) for use in calculating the solute concentration (step 64). This STW device can have a binding layer, but if only viscosity is to be measured, such binding layer is not included.

Figure 7A:
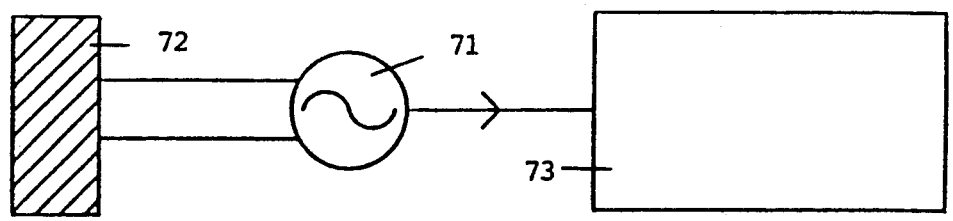
FIGS. 7A-7C illustrate these representative embodiments for converting propagation velocity variation in an STW device to either frequency or phase variation.
Figure 7B:
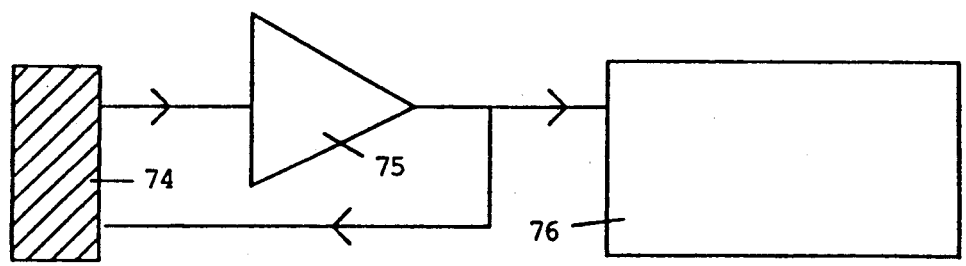
Figure 7C:
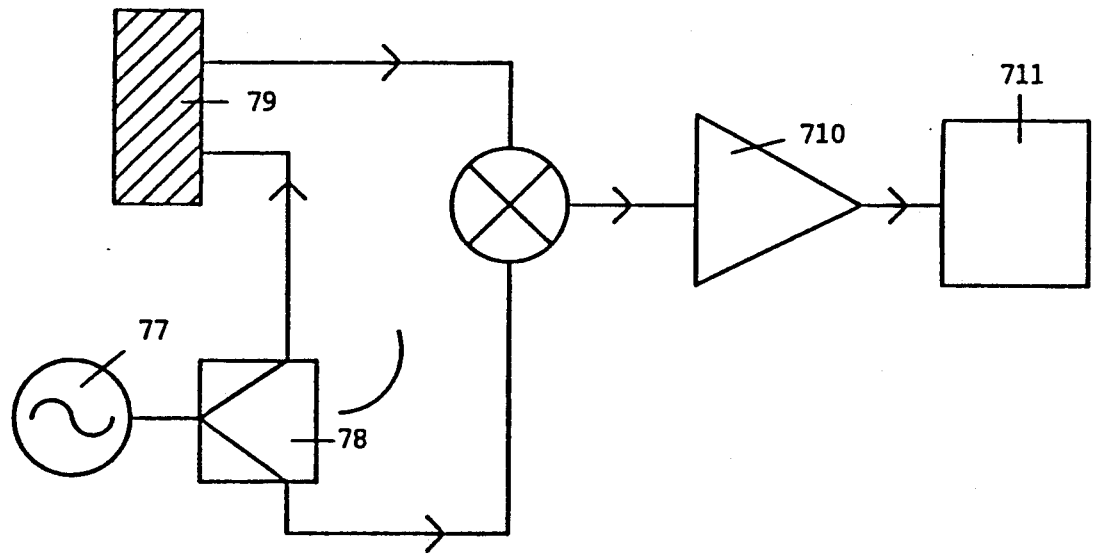

FIGS. 7A and 7B illustrate a pair of embodiments in which the frequency of the output signal indicates the solute concentration in the liquid of the solute that is selectively detected by this STW device. In FIG. 7A, an oscillator 71 is coupled to a one-port STW device 71 that adjusts the frequency of the oscillator. A frequency counter 73, coupled to the oscillator, measures the frequency of the oscillator. In FIG. 7B, a two-port STW device 74 is coupled in a feedback loop with an amplifier 75 and a frequency counter 76 measures the frequency of the signal at the output port of the amplifier. FIG. 76 illustrates a third embodiment in which the phase of the output signal indicates this concentration. In FIG. 7C, an oscillator 77 is connected to an input of a splitter 78. One output of this splitter is connected through a two-port STW device 79. The signals on the other output of this splitter and on an output of the STW device are combined to produce a signal that is applied to an input of an amplifier 710. An output signal from this amplifier is measured by a voltmeter 711 to produce a measure of the phase difference between the signals on the second output of the splitter and the output of the STW device. When the chemical concentration of a class of solutes in the solution is to be determined, in step 61, an STW device having a binding layer 18 that is chemically selective for a class of chemicals to be detected. When the chemical concentration of a particular solute in the solution is to be determined, in step 61, an STW device, having a binding layer 18 that is chemically specific to the solute to be detected, is used.

Figure 8:
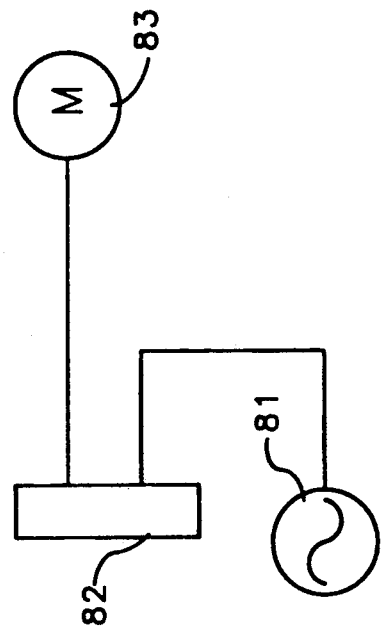
FIG. 8 illustrates an embodiment for measuring liquid viscosity with an STW device.

FIG. 8 illustrates an embodiment suitable for detecting the viscosity of a liquid. The liquid viscosity acts to damp a surface acoustic wave in the STW device. Therefore, the device in FIG. 8 includes a signal source 81 that provides a signal of a known amplitude. This signal is applied to a STW device 82 and the amplitude of an output signal is measured by a meter 83. As is illustrated in FIG. 6, additional steps 61'-63' can be included in the method of measurement to enable subtraction of a reference value of the output signal before calculation in step 64 of the solute concentration or the liquid viscosity. This is particularly useful for viscosity measurements because the small output signal value can contain a baseline correction that is a nonnegligible fraction of the output signal. In steps 61'-63', the STW device is immersed in a reference fluid such as air, a test signal is applied to the input transducer of the STW device and the STW output signal is monitored. These two measured output signal amplitudes are then used in step 64 to calculate the viscosity of the liquid under test.

We claim:

1. A method of measuring properties of a liquid, said method comprising the steps of:

(a) immersing a surface transverse wave device in said liquid, said device having an input, a mechanism for trapping acoustic waves at a top surface of this device that is exposed to said liquid, a crystal cut such that acoustic waves launched from its input are surface transverse waves, and an output;

(b) applying to said input an input signal that excites shear horizontal waves in the surface transverse wave device; and (c) detecting an output signal at said output.

2. A method as in claim 1 wherein step (a) comprises immersing in said liquid a surface transverse wave having no binding layer, said method further comprising the step of:

(d1) calculating the viscosity of the fluid as a function of the output signal.

3. A method as in claim 1, wherein step (a) comprises immersing in said liquid a surface transverse wave device having a surface coated with a binding layer that selectively adheres to a preselected class of solutes that is soluble in said liquid, said method further comprising the step of:

(d2) calculating the concentration of said preselected class of solutes as a function of the output signal.

4. A method as in claim 3, wherein step (a) comprises immersing in said liquid a surface transverse wave device having a surface coated with a binding layer selected from the group consisting of an antigen and its associated antibody, whereby in step (d2) the calculated concentration is the concentration of the other substance in the group.

5. A method as in claim 3, wherein step (a) comprises immersing in said liquid a surface transverse wave device having a surface coated with a binding layer consisting essentially of identical molecules that are each a fragment of a nucleic acid strand, whereby in step (d2) the calculated concentration is the concentration of a nucleic acid strand fragment that is complementary to the fragment in the binding layer.

6. A method as in claim 2 further comprising before step (d1) the steps of:

immersing said surface transverse wave device in a reference fluid;

applying an input signal to said input; and detecting an output signal at said output to measure the output signal while immersed in said reference fluid; and wherein the calculation in step (d1) utilizes both of these measured values of the output signal.

7. A method as in claim 3 further comprising before step (d2) the steps of:

immersing said surface transverse wave device in a reference fluid;

applying an input signal to said input; and detecting an output signal at said output to measure the output signal while immersed in said reference fluid; and wherein the calculation in step (d2) utilizes both of these measured values of the output signal.

8. A surface transverse wave device suitable for use as a sensor in liquids, said device comprising:

a piezoelectric substrate having a top surface;

at least one transducer on said top surface;

a binding layer that binds to a class of solutes to be detected in said liquid; and means for trapping acoustic waves in the substrate at the top surface of said substrate;

said piezoelectric substrate being cut such that, for a given signal excitation, said at least one transducer couples substantially only into shear transverse acoustic waves, whereby this device functions as a surface transverse wave device and exhibits a much greater sensitivity than a SAW device or a surface skimming bulk wave device of comparable dimensions and arrangement of said at least one transducer.

9. A device as in claim 8 further comprising a shielding layer covering said at least one transducer, said shielding layer having sufficient thickness to substantially eliminate shorting of said transducer by said liquids.

10. A device as in claim 9 wherein the transducer has a plurality of parallel, electrically conductive elements separated by a spacing $S_1$ and said shielding layer has a thickness at least on the order of the spacing $S_1$.

11. A device as in claim 8 wherein said binding layer is chemically selective for a selected class of chemicals, whereby said device is a chemical sensor that can measure the concentration of said selected class in said liquid sample.

12. A device as in claim 8 wherein said binding layer is chemically specific for a single chemical, whereby said device is a chemical sensor that can measure the concentration of said single chemical in said liquid sample.

13. A device as in claim 8 further comprising:
means for measuring a change in velocity of a surface transverse wave within said surface transverse wave device, said change being caused by solute particles that bind to said binding layer.

14. A surface transverse wave device suitable for use as a sensor in liquids, said device comprising:
a piezoelectric substrate having a top surface;
at least one transducer on said top surface;
a shielding layer covering said at least one transducer, said shielding layer having sufficient thickness to substantially eliminate shorting of said transducer by said liquids; and
means for trapping acoustic waves in the substrate at the top surface of said substrate,
said piezoelectric substrate being cut such that said at least one transducer couples substantially only into shear transverse acoustic waves, whereby this device functions as a surface transverse wave device and exhibits a much greater sensitivity than a SAW device or a surface skimming bulk wave device of comparable dimensions and arrangement of said at least one transducer.

15. A surface transverse wave device suitable for use as a sensor in liquids, said device comprising:
a piezoelectric substrate having a top surface;
at least one transducer on said top surface; and
means for trapping acoustic waves in the substrate at the top surface of said substrate;
said substrate being cut such that acoustic displacement within this substrate is favored in a direction perpendicular to a direction of wave propagation and parallel to the top surface.

16. A surface transverse wave device as in claim 15 wherein said substrate is quartz and wherein the substrate has been formed by the ST-cut of quartz.

* * * * *